| United States Patent [19] | [11] Patent Number: 4,904,589 |
| Sato et al. | [45] Date of Patent: Feb. 27, 1990 |

[54] PROCESS FOR PRODUCING D-(31)-TARTARIC ACID

[75] Inventors: Haruyo Sato; Shinzo Imamura, both of Aichi, Japan

[73] Assignee: Toray Industries, Inc., Japan

[21] Appl. No.: 247,365

[22] Filed: Sep. 21, 1988

[30] Foreign Application Priority Data

Oct. 16, 1987 [JP] Japan .................................. 62-262024

[51] Int. Cl.$^4$ .......................... C07P 41/00; C12P 7/46; C12P 1/22; C12R 1/40
[52] U.S. Cl. ...................................... 435/145; 435/250; 435/822; 435/852; 435/877
[58] Field of Search ............... 435/145, 280, 852, 877, 435/822

[56] References Cited

U.S. PATENT DOCUMENTS

| 2,314,831 | 3/1943 | Kamlet ................................ 435/145 |
| 2,559,650 | 7/1951 | Lockwood et al. ................. 435/145 |
| 3,600,279 | 8/1971 | Takabashi et al. . |
| 3,957,579 | 5/1976 | Sato et al. .......................... 435/145 |
| 4,011,135 | 3/1977 | Kamatani et al. ................... 435/145 |
| 4,028,185 | 6/1977 | Kamatani et al. ................... 435/145 |
| 4,092,220 | 5/1978 | Tsurumi et al. ..................... 435/145 |
| 4,204,044 | 5/1980 | Suhara et al. ....................... 435/280 |
| 4,520,106 | 5/1985 | Kado .................................. 435/172.3 |

FOREIGN PATENT DOCUMENTS 24490 3/1975 Japan .

OTHER PUBLICATIONS

Chemical Abstracts, vol. 83, No. 9, Sep. 1, 1975, p. 509 Abstract $\pi 7/003z$.

Primary Examiner—Herbert J. Lilling
Attorney, Agent, or Firm—Austin R. Miller

[57] ABSTRACT

It is possible to efficiently obtain D-(31)-tartaric acid in high yield and to supply DL-tartaric acid of high concentration to the culture medium by cultivating a microorganism which belongs to the genus Pseudomonas, Cryptococcus, Tricosporon or Klebsiella and has an ability to assimilate L-(+)-tartaric acid and does not assimilate substantially D-(−)-tartaric acid in a culture medium containing DL-tartaric acid.

13 Claims, No Drawings

PROCESS FOR PRODUCING D-(31)-TARTARIC ACID

BACKGROUND OF THE INVENTION (1) Field of the Invention

The present invention relates to a process for industrially producing D-(—)-tartaric acid.

(2) Description of the Prior Art

A process for producing biochemically D(—)-tartaric acid comprising cultivating the genus Aerobacter in DL-tartaric acid and obtaining D-(—)-tartaric acid from the culture broth, has been already known (Japanese Unexamined Patent Publication No. 24490/1975).

However, in the prior art, the yield of D-(—)-tartaric acid is low (at most 88%), and the cultivating time is long (33 hours or more). Moreover, the concentration of DL-tartaric acid, which is a raw material to be added in the cultivating medium, is low (4%). Therefore, the prior art is not an industrially favorable process.

SUMMARY OF THE INVENTION

One purpose of the present invention is to propose a process for obtaining D-(—)-tartaric acid in high yield, namely in almost theoretically quantitative amounts from DL-tartaric acid by means of a selective assimilation method using a microorganism.

Another purpose of the present invention is to propose a process for obtaining D-(—)-tartaric acid in high yield by supplying a high concentration of DL-tartaric acid to a culture medium without obstructing the growth of microorganisms and without decreasing the ability of selective decomposition.

The other purpose of the present invention is to propose an efficient process in which cultivating microorganisms assimilating a half of DL-tartaric acid can be carried out in a short time.

Other and further objects, features, and advantages of the present invention will appear more fully from the following description.

These purposes can be achieved by a process for producing D(—)-tartaric acid characterized by cultivation of a microorganism which belongs to the genus Pseudomonas, Cryptococcus, Tricosporon, or Klebsiella and has an ability to assimilate L-(+)-tartaric acid and does not substantially assimilate D-(—)-tartaric acid, decomposing asymmetrically thereby L-(+)-tartaric acid and obtaining remaining D(—)-tartaric acid from the culture broth.

DESCRIPTION OF THE PREFERRED EMBODIMENTS

As the microorganism used in the present invention, microorganisms belonging to the genus Pseudomonas, Cryptococcus, Tricosporon, or Klebsiella can be employed. Among these microorganisms, such microorganisms that have an ability to assimilate L-(+)-tartaric acid and do not substantially assimilate D-(—)-tartaric acid can be used in the present invention.

In the present invention, microorganisms which do not substantially assimilate D-(—)-tartaric acid include (A) such microorganisms that assimilate only small amounts of D-(—)-tartaric acid, within the extent that the effect of the present invention is not substantially obstructed, and (B) such microorganisms that assimilate D-(—)-tartaric acid without existence of L-(+)-tartaric acid after almost all L-(+)-tartaric acid has been assimilated.

For example, *Pseudomonas putida* ATCC 17642, *Psuedomonas putida* ATCC 15070, *Psuedomonas fluorescens* ATCC 17634, *Cryptococcus lourentii* ATCC 36832, *Cryptococcus lourentii* TORAY 2002 FERM BP-2021, *Tricosporon cutaneum* ATCC 36993, *Tricosporon cutaneum* TORAY 2035 FERM BP-2022, *Klebsiella pneumoniae* ATCC 21316, and *Klebsiella pneumoniae* ATCC 12658 are employed.

*Pseudomonas putida* ATCC 17642, *Pseudomonas putida* ATCC 15070 and *Tricosporon cutaneum* ATCC 36993 were deposited in the American Type Culture Collection, 12301 Parklawn Drive, Rockville, Md. 20852-1776 under the Budapest Treaty. *Tricosporon cutaneum* FERM BP-2022 was deposited in the Fermentation Research Institute Agency of Industrial Science & Technology, at No. 1-3, Yatabe-cho, Higashi 1-chome, Tsukuba-gun, Ibaragi-ken, 305 Japan under the Budapest Treaty.

The concentration of DL-tartaric acid in a medium is ordinarily 1 to 300 g/l, preferably 30 to 150 g/l, more preferably 50 to 150 g/l. When the concentration of DL-tartaric acid is low, the productive efficiency becomes worse. On the other hand, when the concentration is high, the cultivation time becomes longer, and the growing of the microorganisms is arrested in some cases.

The total amount of DL-tartaric acid can be fed in the culture medium from the beginning or fed dividedly in several times.

The cultivation can be carried out in a wide range of pHs. The culture medium is usually adjusted to pH of 5 to 7 when the cultivation starts. The pH increases as the cultivation proceeds, but the cultivation can be further carried out in that condition. To shorten the cultivation time, it is preferable to add an acid during the cultivation in accordance with the increase in pH. The pH during cultivation depends on the microorganism and is adjusted preferably to 5 to 8, more preferably to 5.5 to 7.

As the acid added during cultivation, for example, an aqueous solution of an inorganic acid such as phosphoric acid, sulfuric acid, hydrochloric acid and so on is preferable.

The cultivation temperature is usually 20° to 40° C., preferably 25° to 35° C. The cultivation is carried out with stirring and aeration. The amount of aeration is usually 0.5 to 2.0 vvm, preferably 0.7 t 1.5 vvm. If the amount of aeration is too small, there is a tendency that the assimilating speed of L-(+)-tartaric acid becomes slow. If it is too large, the effect does not change, and it is not desirable that the concentration of the culture medium becomes higher and foaming vigorously occurs because vaporization of the culture medium is rather accelerated.

After L-(+)-tartaric acid has been completely consumed, D-(—)-tartaric acid is separated by means of a usual method.

Namely, after the cultivation is finished, the microorganism is removed by centrifuging the culture broth and calcium chloride is added to separate calcium D-(—)-tartarate as a precipitate.

Sulfuric acid is added in calcium D-(—)-tartarate to precipitate calcium sulfate and D-(—)-tartaric acid is separated in water. D-(—)-tartaric acid can be obtained by concentrating the aqueous solution. Refined D-(—)- tartaric acid can be obtained by recrystallizing from water.

The present invention will be more clearly understood with reference to the following Examples.

EXAMPLE 1

3 g of bouillon were dissolved in 100 ml of water and the solution was put in an 1 liter Erlenmeyer flask and sterilized at 120° C. for 20 minutes. One platinum loop of *Pseudomonas putida* ATCC 17642 was inoculated into the medium and cultivated with shaking at 30° C. for 17 hours to obtain a culture broth.

80 g of DL-tartaric acid, 12 g of ammonium chloride, 0.6 g of magnesium sulfate 7 hydrate, 0.6 g of calcium chloride, 0.15 g of ferric chloride 6 hydrate, 10 g of dipotassium hydrogenphosphate and 2.0 g of yeast extract were dissolved in 1,100 ml of water and the pH was adjusted to 7.0 with 6 N sodium hydroxide aqueous solution. This culture medium was put into a 3 liter minijar fermenter and sterilized at 120° C. for 20 minutes.

The above described culture broth was put in this culture medium and cultivated at 30° C. for 30 hours with aeration and the pH of the mixture was kept in the range of 7 to 7.1 with 2 N hydrochloric acid. The value of Optical Density in 550 mμ ($OD_{550}$) was 6.7, when the cultivation was completed.

The cells were removed by centrifuging the culture broth at 10,000 G for 10 minutes. 35.8 g of calcium chloride were added in the supernatant liquid, which was then stirred at room temperature for one hour. Deposited crystalline was filtered and dried under reduced pressure to obtain 65.3 g of calcium D-(−)-tartarate 4 hydrate. The yield was 94.2%.

52.04 g of calcium D-(−)-tartarate 4 hydrate whose $[\alpha]_D$ was −5.4° (C=4, 0.1 N HCl), was suspended in 300 ml of water and 100 ml of 4 N sulfuric acid solution was added under stirring and stirred at room temperature for 3 hours.

After the precipitate was separated by means of filtration, the filtrate was concentrated under reduced pressure and dried under reduced pressure to obtain 30.8 g of crude D-(−)-tartaric acid. The yield was almost quantitative.

$[\alpha]_D$ was −12.8° (C=4.0 $H_2O$)

By recrystallizing from water, D-(−)-tartaric acid of rod-like crystalline was obtained.

$[\alpha]_D$ was −14.1° (C=4.0, $H_2O$)

EXAMPLE 2

In the same way as shown in Example 1, utilizing *Pseudomonas putida* ATCC 17642, 40 g of DL-tartaric acid was put in the culture medium and the cultivation was carried out without adding hydrochloric acid. All L-(+)-tartaric acid was consumed in 8.5 hours and 19.8 g of D-(−)-tartaric acid was obtained. The value of $OD_{550}$ was 5.1.

EXAMPLE 3

3 g of bouillon was dissolved in 100 ml of water and the solution was put in a 1 liter Erlenmeyer flask and sterilized at 120° C. for 20 minutes. One platinum loop of *Cryptococcus laurentii* ATCC 36832 was inoculated on this medium and cultivated with shaking at 30° C. for 17 hours to obtain a culture broth.

80 g of DL-tartaric acid, 12 g of ammonium chloride, 0.6 g of magnesium sulfate 7 hydrate, 0.6 g of calcium chloride, 0.15 g of ferric chloride 6 hydrate, 10 g of dipotassium hydrogenphosphate and 2.0 g of yeast extract were dissolved in 1,100 ml of water and the pH was adjusted to 7.0 with 6 N sodium hydroxide aqueous solution. This culture medium was put in a 3 liter minijar fermenter and sterilized at 120° C. for 20 minutes.

The above described culture broth was put in this culture medium and cultivated at 30° C. for 40 hours with aeration and the pH of the mixture was kept in the range of 5.0 to 5.5 with 2 N hydrochloric acid.

The cells were removed by centrifuging the culture broth at 10,000 G for 10 minutes. 35.8 g of calcium chloride was added in the supernatant liquid, which was then stirred at room temperature for one hour. Deposited crystalline was filtrated and dried under reduced pressure to obtain 64.1 g of calcium D-(−)-tartrate 4 hydrate. The yield was 92.5 %.

$[\alpha]_D$ was −5.4° (C=4.0, 1 N HCl).

64.1 g of calcium D-(−)-tartarate 4 hydrate was suspended in 300 ml of water and 100 ml of 4 N sulfuric acid aqueous solution were added under stirring at room temperature for 3 hours.

After the precipitate was separated by means of filtration, the filtrate was concentrated under reduced pressure and dried to obtain 45.1 g of crude D-(−)-tartaric acid. The yield from calcium D-(−)-tartarate 4 hydrate was 100%.

$[\alpha]_D$ was −12.5° (C=4.0, $H_2O$)

By recrystallizing it with water, D-(−)-tartaric acid of rod-like crystalline was obtained.

$[\alpha]_D$ was −14.1° (C=4.0, $H_2O$)

EXAMPLES 4 and 5

In the same way as shown in Example 1, 40 g of DL-tartaric acid was put in the culture broth and *Tricosporon cutaneum* ATCC 36993 and *Klebsiella pneumoniae* ATCC 21316 were inoculated respectively in the same way as shown in Example 1 and the cultivations were carried out. L-(+)-tartaric acid was completely consumed after 15 to 20 hours and 19.2 g and 19.3 g of D-(−)-tartaric acid were obtained respectively. The yields of D-(−)-tartaric acid were accordingly 96% and 96.5%, respectively.

The ratio of tartaric acid was analyzed by high performance liquid chromatography (HPLC) after reaction with 3,5-dinitrophenylisocyanate.

| The conditions of HPLC | |
|---|---|
| Column | YMC-A-KO3 |
| Mobile phase | n-Hexane/1,2-dichloroethane/Ethanol = 51/30/19 |
| Flow rate | 0.7 ml/min |
| Detector | UV 254 nm |
| Retention time | L structure 10.43' |
|  | D structure 17.58' |

EXAMPLES 6 and 7

5 ml of culture medium containing 30 g/l of dried bouillon were put in 18 mmφ test tubes and sterilized.

Microorganisms shown in Table 1 were inoculated and cultivated with shaking at 30° C. for 24 hours.

10 g of DL-tartaric acid, 1.0 g of ammonium chloride, 0.2 g of magnesium sulfate 7 hydrate, 0.2 g of calcium chloride, 0.05 g of ferric chloride 6 hydrate, 3.0 g of dipotassium hydrogenphosphate and 0.5 g of yeast extract were dissolved in 1 liter of water and adjusted to pH 7 with sodium hydroxide.

5 ml of this culture medium were put in 18 mmφ test tubes and sterilized. 0.1 ml of the above described culture broth was therein added under sterile conditions. After cultivated with shaking at 30° C. for 24 hours, the cells were removed and 20 m g of calcium chloride were added in the supernatant liquid. Deposited crystalline was filtrated. DL analysis of this crystalline was carried out by HPLC and the ratios of L and D of tartaric acid were shown in Table 1.

EXAMPLE 8 and 9

5 ml of culture medium of species containing 30 g/l of bouillon were put in 18 mmφ test tubes and sterilized. Microorganisms shown in Table 1 were inoculated thereon and cultivated with shaking at 30° C. for 24 hours.

0.1 ml of the above described culture broth were added in the culture medium adjusted at pH 5 in the same way as shown in Example 6 under sterile conditions. The following procedures are carried out in the same way as those of Examples 6 and 7 and the ratios of L and D structures were obtained. The results were shown in Table 1.

TABLE 1

| Example | Strain | Remainder of L-Structure (%) | Remainder of D-Structure (%) |
|---|---|---|---|
| 6 | Pseudomonas putida ATCC 15070 | 3.6 | 93.2 |
| 7 | Klebsiella pneumoniae ATCC 12658 | 1.2 | 71.0 |
| 8 | Cryptococcus laurentii TORAY2002 FERM-BP 2021 | 2.7 | 81.0 |
| 9 | Tricosporon cutaneum TORAY2035 FERM-BP 2022 | 3.2 | 98.8 |

What we claim is:

1. A process for producing D-(−)-tartaric acid characterized by cultivating a microorganism which belongs to the genus *Pseudomonas putida,* or Tricosporon, and has an ability to assimilate L-(+)-tartaric acid and does not assimilate substantially D-(−)-tartaric acid, decomposing asymmetrically thereby L-(+)-tartaric acid and separating and obtaining remaining D-(−)-tartaric acid from the culture broth.

2. A process according to claim 1, wherein said microorganisms belonging to the genus Tricosporon are microorganisms which belong to *Tricosporon cutaneum.*

3. A process according to claim 1, wherein said Pseudomonas microorganism is *Pseudomonas putida* ATCC 17642.

4. A process according to claim 1, wherein said Pseudomonas microorganism is *Pseudomonas putida* ATCC 15070.

5. A process according to claim 1, wherein said Tricosporon microorganism is *Tricosporon cutaneum* FERM BP-2022.

6. A process according to claim 1, wherein said Tricosporon microorganism is *Tricosporon cutaneum* ATCC 36993.

7. A process for producing D-(−)-tartaric acid cultivating a microorganism which belongs to the genus Cryptococcus or Klebsiella, and has an ability to assimilate L-(+)-tartaric acid and does not assimilate substantially D-(−)- tartaric acid, decomposing asymmetrically thereby L-(+)-tartaric acid and separating and obtaining remaining D-(−)-tartaric acid from the culture broth.

8. A process according to claim 7, wherein said microorganisms belonging to the genus *Cryptococcus laurenti.*

9. A process according to claim 7, wherein said Cryptococcus microorganism is *Cryptococcus laurenti* ATCC 36832.

10. A process according to claim 7, wherein said Cryptococcus microorganism is *Cryptococcus laurenti* FERM BP-2021.

11. A process according to claim 7, wherein said microorganisms belonging to the genus Klebsiella are microorganisms which belong to *Klebsiella pneumoniae.*

12. A process according to claim 7, wherein said Klebsiella microorganism is *Klebsiella pneumoniae* ATCC 21316.

13. A process according to claim 7, wherein said Klebsiella microorganism is *Klebsiella pneumoniae* ATCC 12658.

* * * * *